United States Patent [19]

Franicevic

[11] Patent Number: 5,498,231
[45] Date of Patent: Mar. 12, 1996

[54] INTUBATING LARYNGOSCOPE

[76] Inventor: Klaus Franicevic, 1531 SE. 12th St., Deerfield Beach, Fla. 33441

[21] Appl. No.: 206,404
[22] Filed: Mar. 7, 1994
[51] Int. Cl.⁶ .................................................. A61B 1/267
[52] U.S. Cl. ....................... 600/190; 600/194; 600/196; 600/199; 600/237; 128/200.26; 128/207.14
[58] Field of Search .................... 128/10, 11, 15, 128/16, 17, 18, 20, 200.26, 207.14, 207.15, 911

[56] References Cited

U.S. PATENT DOCUMENTS

| | | | |
|---|---|---|---|
| 1,568,732 | 1/1926 | Haslinger . | |
| 2,127,215 | 8/1938 | Gwathmey | 128/207.14 |
| 3,677,262 | 7/1972 | Zukowski . | |
| 3,754,554 | 8/1973 | Felbarg . | |
| 4,314,551 | 2/1982 | Kadell | 128/11 |
| 4,793,327 | 12/1988 | Frankel | 128/207.14 X |
| 4,832,004 | 5/1989 | Heckele | 128/10 |
| 5,016,614 | 5/1991 | MacAllister | 128/207.14 X |
| 5,092,314 | 5/1992 | Zeitels | 128/10 |
| 5,261,392 | 11/1993 | Wu | 128/11 |
| 5,327,881 | 7/1994 | Greene | 128/11 |

FOREIGN PATENT DOCUMENTS

| | | | |
|---|---|---|---|
| 3217476 | 12/1982 | Germany | 128/17 |
| 175169 | 12/1965 | U.S.S.R. . | |

Primary Examiner—Richard J. Apley
Assistant Examiner—Kelly McGlashen

[57] ABSTRACT

A laryngoscope for use in difficult intubation due to malformation of the jaws, tongue, pharynx, larynx or neck as a result of trauma, edema, inflammation or congenital anomalies. An elongate hollow body terminates in a pair of opposed blades perpendicular to the said hollow body being pivotal on two axes. The endotracheal tube used for the intubation rides within the hollow tube on the introducing means disposed in the cavity of the said hollow body. Light conducting means illuminate the larynx and optical means are provided for inspecting the larynx during the intubation procedure.

8 Claims, 5 Drawing Sheets

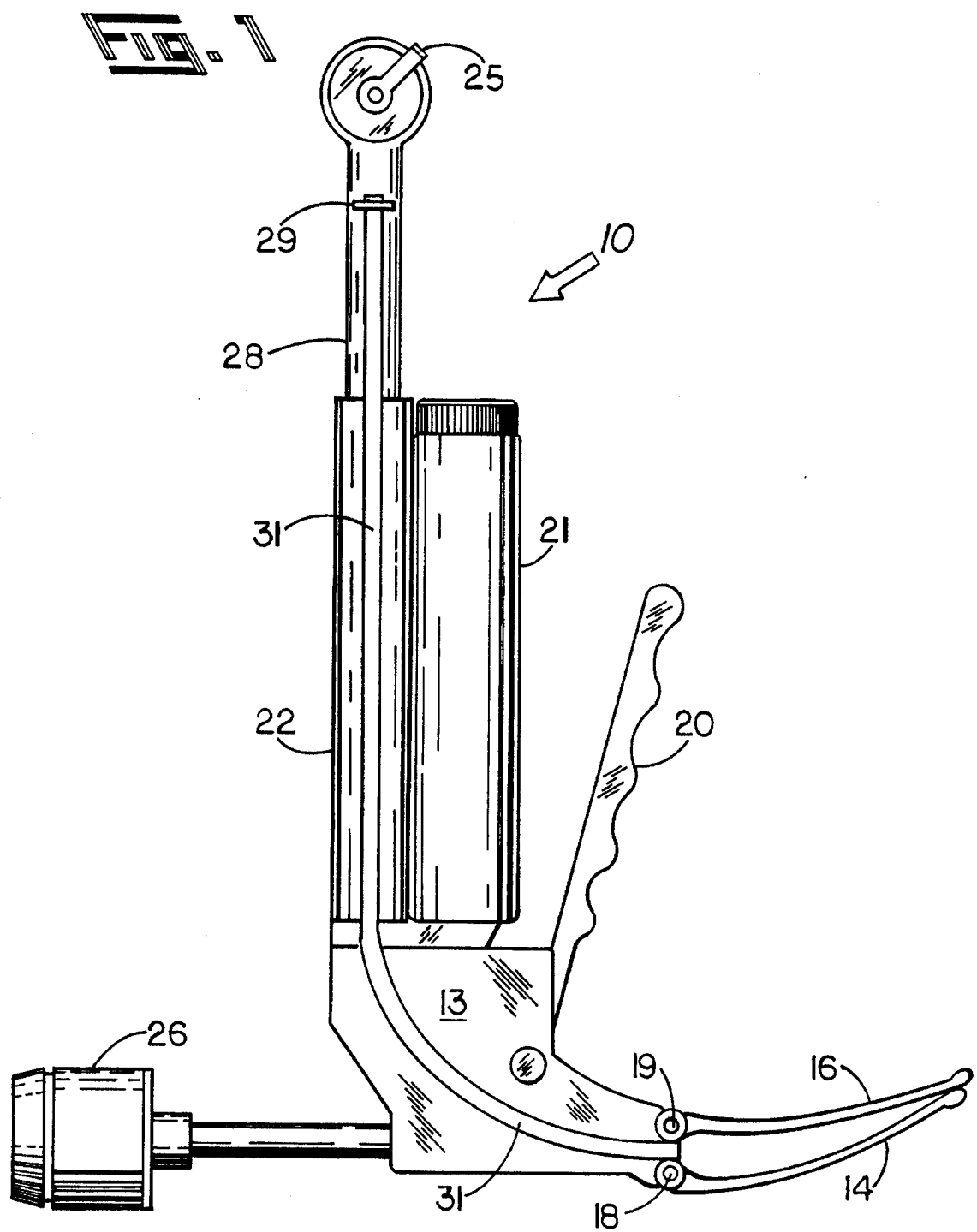

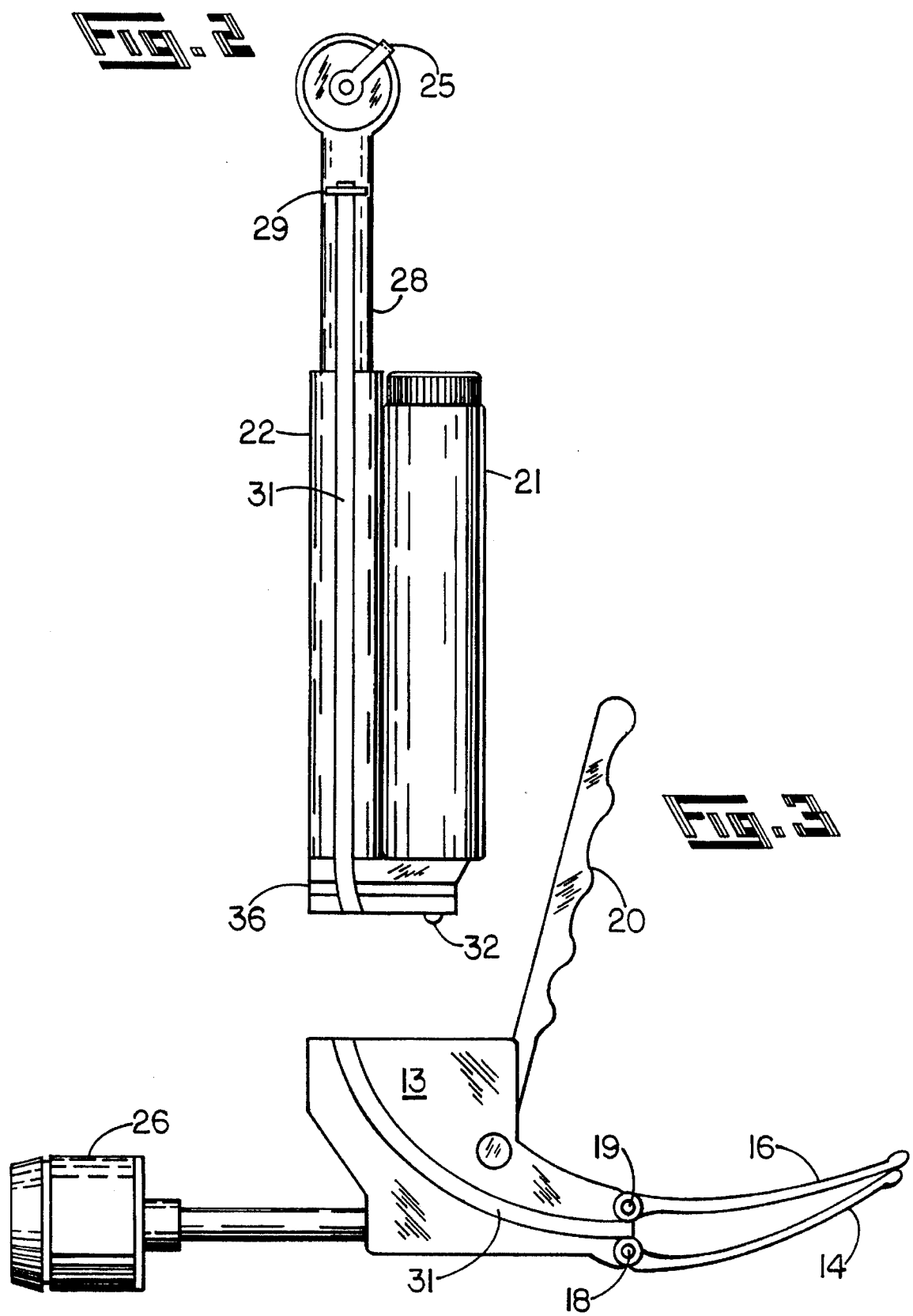

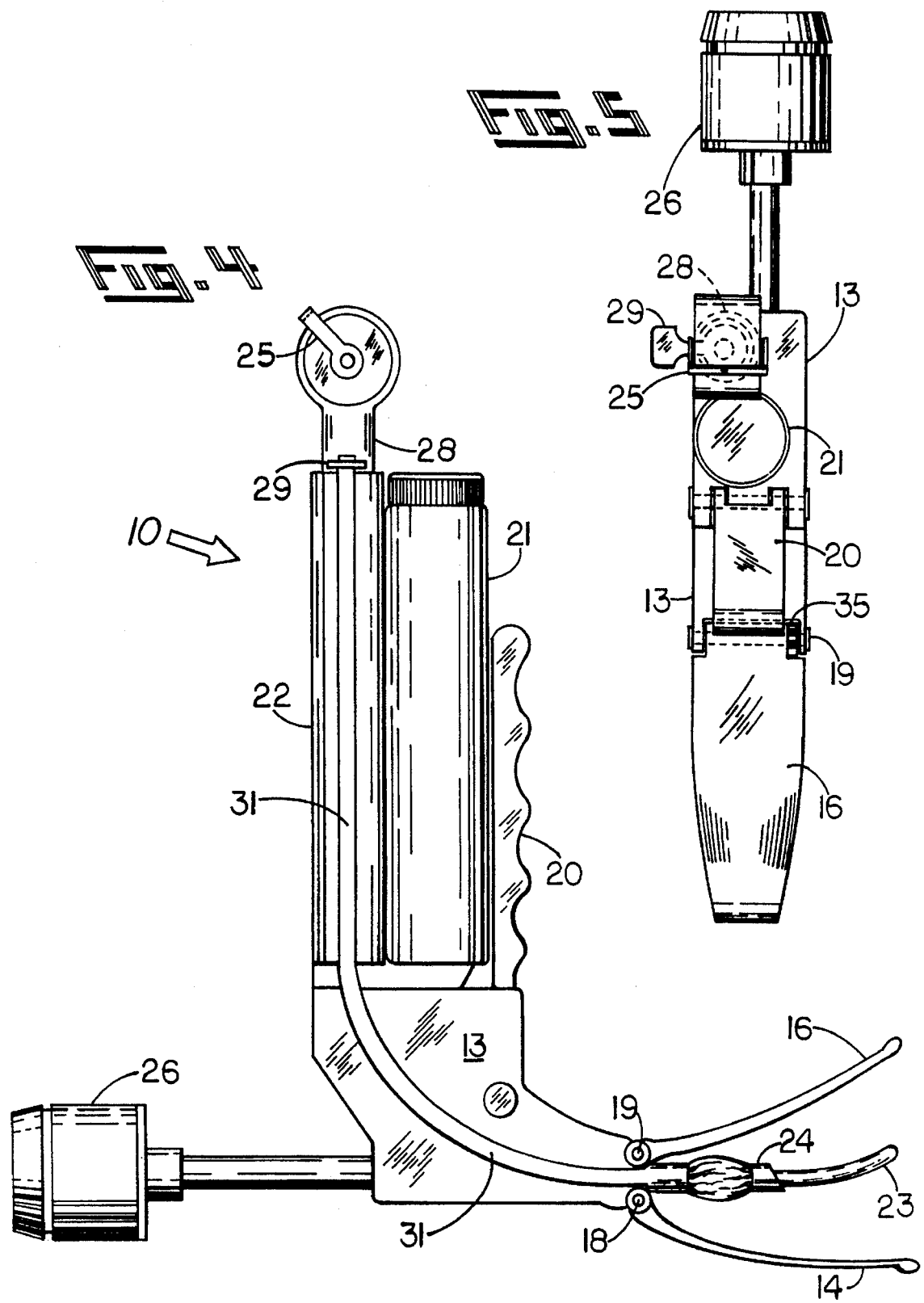

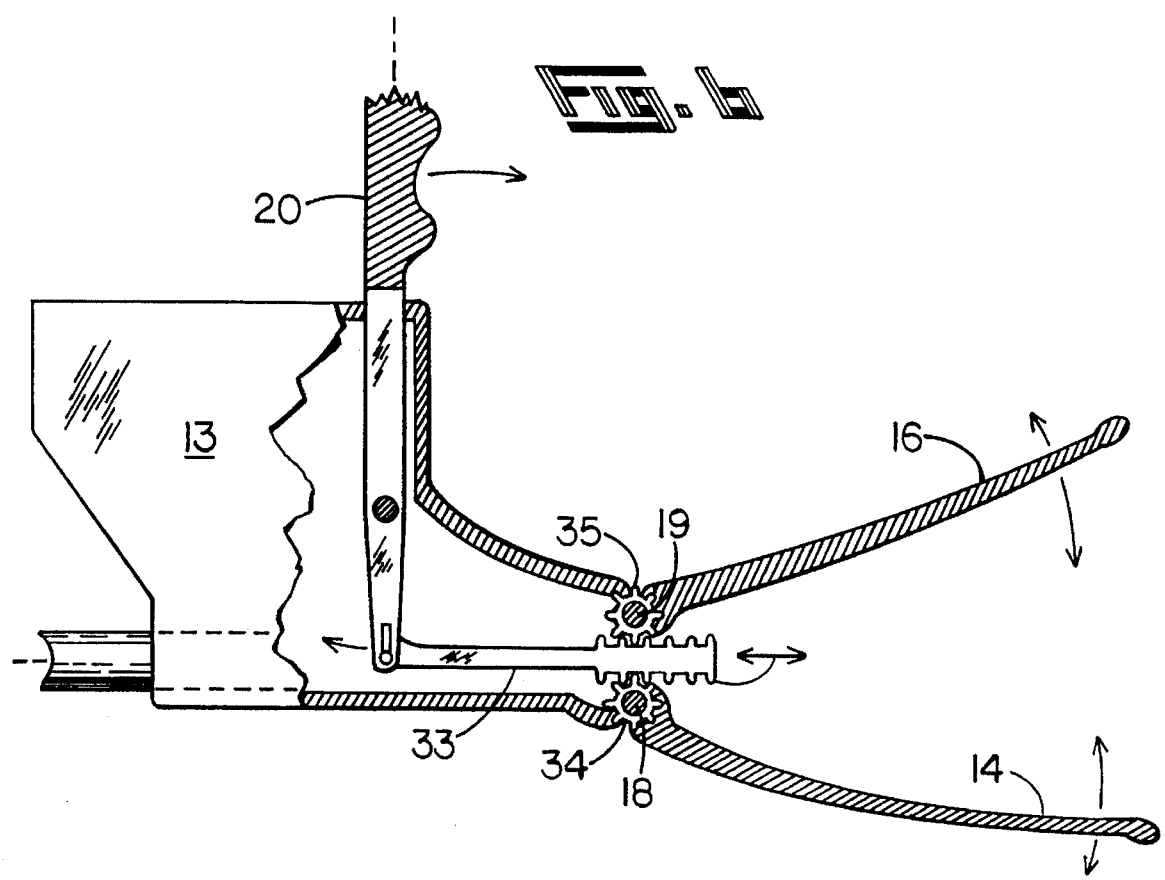

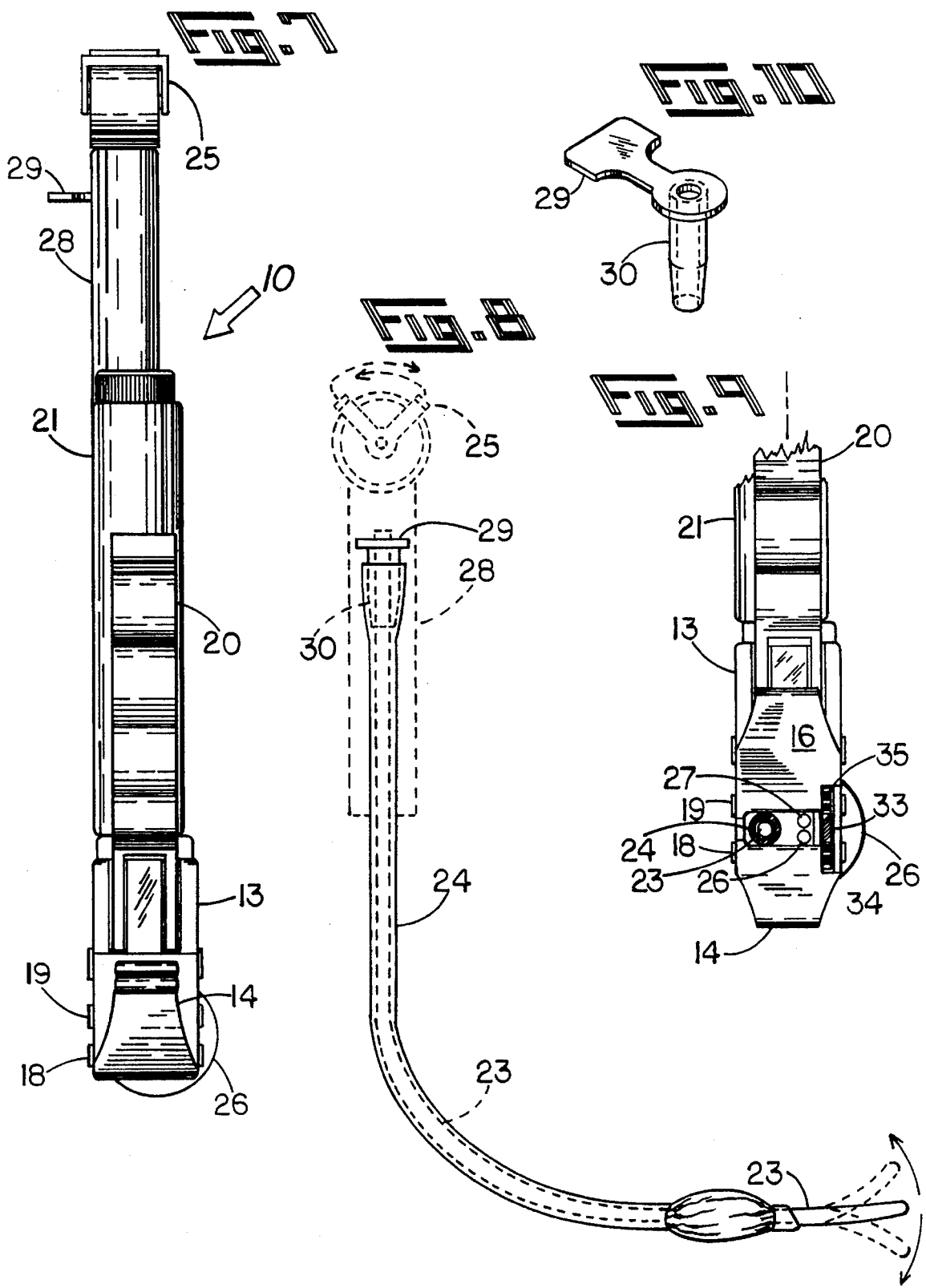

INTUBATING LARYNGOSCOPE

BACKGROUND OF THE INVENTION

1. Field of the Invention

This invention relates generally to surgical instruments, and more particularly relates to laryngoscopes having opposed blades on distal end thereof.

2. Description of the Prior Art

In anesthesiology, the laryngoscope is used for endotracheal intubation. A rubber or plastic tube is introduced through the larynx into the trachea under direct or indirect optical control.

Earlier laryngoscopes, such as the MacIntosh or Foregger have only one blade. The blade may be strait or curved and is fixedly secured to a hollow handle which houses the batteries. A lamp for providing light for the direct laryngoscopy is mounted on the blade. No optical system was provided.

These earlier laryngoscopes can be introduced orally and used properly only if the patient's mouth is fully opened. If the patient's mouth is fully opened, then the sole blade can slide from the teeth and tongue to the pharynx, pulling or pushing the epiglottis and thus expose the entrance of the larynx.

Intubation is difficult or impossible for those patients with abnormalities, whose mouth could not be fully opened.

In recent times a trial was made to produce laryngoscopes with optical systems to be used in difficult intubations. These newer instruments are not very practical and are not a real progress in anesthesiology.

| Laryngoscopes and similar instruments for endotracheal intubation patented earlier: | | |
|---|---|---|
| Inventor | Patent No. | Year |
| F. Haslinger (U.S.A.) | 1,568,732 | 1926 |
| D. T. Atkinson (U.S.A.) | 1,607,788 | 1926 |
| A. S. Pogosyan (U.S.S.R.) | 898,849/31-16 | 1964 |
| H. J. Zukowski (U.S.A.) | 3,677,262 | 1972 |
| H. Feldbarg (U.S.A.) | 3,754,554 | 1973 |
| L. Lepelletier (France) | 2,361,855 | 1976 |
| J. A. Moses (U.S.A.) | 4,114,609 | 1977 |
| J. R. Bullard (U.S.A.) | 4,086,919 | 1978 |
| K. Storz (U.S.A.) | 4,294,235 | 1981 |

SUMMARY OF THE INVENTION

The deficiencies of the existing laryngoscopes are overcome by a laryngoscope having a hollow body terminating in a pair of opposed blades. At least one of the blades is pivotal about an axis so that the blades may assume a closed beak position or an opened beak position or, of course, any position there in between. When the opposed blades are in the closed beak position, the laryngoscope may be introduced into the patient's mouth that is only minimally opened. After the introduction, the distal end of the blades are moved apart into the open beak position without the necessity to further open the patient's mouth. Preferably, the movable blades pivot about their axes thereby pressing against the base of the tongue and the soft palate creating a large space where all details of larynx could be observed without obstruction even in major malformations. Disposed between the blades and extending from the elongate hollow body of the laryngoscope, are a tube introducer, a light conducting system and an optical system. The larynx is observed through an objective disposed at the distal end of the optical system.

It is therefore seen to be an important object of the invention to provide a laryngoscope for use with patients with anomalies of the jaws, tongue, larynx or neck, or where the mouth could not be opened fully or where the viewing and reaching of the larynx is difficult or impossible.

Another object of the invention is to provide a laryngoscope having at least one light conducting means for illuminating the larynx during the intubation procedure.

Still another object is to provide an endotracheal tube riding on a flexible and steerable tube introducing member that is fixed in the steering mechanism in the proximal end of the handle of the laryngoscope. The introducing member is located in its hollow tube of the handle and disposed between the opposite blades of the laryngoscope on its distal end.

BRIEF DESCRIPTION OF THE DRAWINGS

Further objects and advantages of the present invention will become apparent as the following description proceeds, taken in conjunction with the accompanying drawings in which:

FIG. 1 is a side plan,

FIG. 2 is a side plan showing the disconnected upper part of the laryngoscope, FIG. 3 is showing the side plan of the disconnected lower part of the laryngoscope, FIG. 4 is showing the side plan of the laryngoscope with dilated blades and extended and flexed introducer, FIG. 5 is a plan of the longitudinal view from the proximal end of the laryngoscope, FIG. 6 is the side plan, partially cut away view of one embodiment illustrative of the invention, FIG. 7 is the frontal plan of the laryngoscope, FIG. 8 is showing the introducer and its steering and moving mechanism together with the endotracheal tube, FIG. 9 is the frontal plan showing the details between the blades in open position, FIG. 10 is the frontal plan of the connector between the endotracheal tube and the Y-piece of the anesthesia machine.

DETAILED DESCRIPTION OF THE PREFERRED EMBODIMENT

FIG. 1 shows an illustrative embodiment of the laryngoscope. It comprises an elongate hollow laryngoscope body 10, two blades, inferior 14 and superior 16. The blades are forming a right angle to the body of the laryngoscope. A lever causes the movable blades 14 and 16 to pivot about the axes 18 and 19. As the distance between the lever 20 and the laryngoscope body 10 is narrowed, the distance between the free ends of the blades 14 and 16 is increased. The hollow laryngoscope body consists of two tubes, the anterior 21 is the place for the batteries, the posterior 22 is the receptacle for the introducer 23 and the endotracheal tube 24. Also contained within the anterior tube 21 are the light emitting source and light conducting system with the optical fibres for illuminating the larynx region. The optical system, generally designated 26, is positioned in lower, distal portion of the laryngoscope body 10, parallel to the blades 14 and 16 and perpendicular to the body 10. It has a system of lenses for forming an image on the ocular of the optical system 26 so that the physician can observe the target larynx and the progress of the introducer 23 and the endotracheal tube 24 into the trachea during the intubating performance.

If the patient can fully open his or her mouth, and no major anomalies of the jaws, pharynx, tongue, neck and larynx are present, the laryngoscopes conceived earlier are usually adequate because the physician can observe the larynx directly. Should this for many reasons be not possible, the new laryngoscope could be the perfect tool for a difficult intubation. It has united the good viewing, illumination, space creating and tube steering for a successful placement of the tube 24 into the trachea during the intubation performance.

The introducer 23 and its lever 25 are basically constructed like the conventional flexible bronchoscope. By moving the lever 25 forward, pivoting on its axis, the tip of the introducer 23 bends down and vice versa, when the lever 25 is moved backward the tip of the introducer 23 bends up. By turning the proximal end of the tube 28 left or right, the tip of the introducer follows left or right. By pushing or pulling the proximal end of the tube 28 the introducer 23 moves along and inside the posterior tube 28 and 22, forward or backward. Thus, any location of the entrance to the larynx could be reached.

Technically the bending of the tip of the introducer 23 as well as in conventional bronchoscopes, is achieved by moving the lever 25 pivotally on its axis. This action is transferred over a wheel to its connections with two wires located and embedded each in a longitudinal half of the plastic, flexible body of the introducer 23. These wires are freely gliding in the body of the introducer except on its tip where the wires are connected and fixed. If one wire is pulled and the other pushed with the help od the lever 25 and its wheel, the tip of the introducer 23 is bending.

An elongate slot 31 is formed in the laryngoscope body 10 to allow the movement of the endotracheal tube connector 30 and its protrusion 29 together with the tube 24 on the introducer 23 into the trachea. Thus, it is seen that a total of three levers must be manipulated by the physician to perform the intubation procedure.

The intubation is performed with the new laryngoscope as follows: First, the laryngoscope body 10 is held with the left hand and the laryngoscope blades 14 and 16 in "closed beak" position are introduced into the mouth of the patient and, reaching the right position in the valecula, the left hand holding the laryngoscope body 10 moves the lever 20. This action opens the "beak", creating a free space in the pharynx and the larynx could be easily observed with the optical system 26 and good illumination with the system 27. The right hand is steering the introducer 23 by changing the direction of its tip with the lever 25. Simultaneously the right hand is holding the upper end of the posterior tube 28 pushing it downward. This action brings the telescopic part of the posterior tube 28 into the distal part 22, and the introducer 23, with the endotracheal tube 24 riding on it, down and between the open blades 14 and 16 into the larynx. The right hand then pushes the tube connector 30, holding the protrusion 29, along the slot 31. With this movement the endotracheal tube 24 is brought deeper to its optimal position. The left hand is releasing then the lever 20 and the "beak" is almost closed. The left hand pulls then the laryngoscope body 10 and takes the blades 14 and 16 out of the mouth. In the same time the right hand is holding the endotracheal tube 24 in place, by holding the protrusion 29 of the tube connector 30.

A bias mechanism, such as a spring (not shown) is employed to keep the laryngoscope blades 14 and 16 in the closed "beak" position when the lever 20 is not moved. The movement of the lever 20 is transferred to a rack 33 and pinions 34 and 35 and also to the both blades 14 and 16 rotating on axes 18 and 19. Although these mechanical means have been described, it is understood that electrical or pneumatical means could also be employed.

FIG. 2 represents the detached upper part of the laryngoscope body 10 comprising the anterior tube 21 as housing for the batteries and the posterior tube 22 as housing for the introducer 23 and its steering mechanism 25. As the upper part of the laryngoscope body 10 is detached from the lower part of the laryngoscope body 13, the connecting rail 36 and the arresting knob 32 become visible.

FIG. 3 represents the detached lower part of the laryngoscope body 10 generally designated 13, comprising the optical system 26 and the blades 14 and 16 as well as the lever 20 and its mechanism for the movement of the blades 14 and 16. This detachment is necessary for it makes possible to sterilise the contaminated part of the laryngoscope. The detachment makes also possible to use different sizes of the blades 14 and 16 if necessary.

FIG. 4 represents the same lateral view of the laryngoscope as on FIG. 1 but with the lever 20 moved to the body of the laryngoscope 10 and, as the result of this movement the separation of the distal ends of the blades 14 and 16. The telescopic part of the posterior tube 28 is moved into the body of the laryngoscope 10, described as the posterior tube 22. The movement of the telescopic part of the posterior tube 28 into the fixed tube 22 slides the introducer 23 between the blades 14 and 16.

FIG. 5 is the view of the laryngoscope from its proximal end, showing the steering mechanism 25 of the introducer 23, the protrusion lever 29 of the endotracheal tube connector 30, the lever 20 for moving the blades 14 and 16, and the upper blade 16 as well as the optical system 26.

FIG. 6 shows in detail how the movement of the lever 20 is transferred to the axes 18 and 19 and to the blades 14 and 16 over the rack 33 and pinions 34 and 35.

FIG. 7 represents the frontal view of the laryngoscope with the extended telescopic part 28 out of the posterior tube (not visible), the protruding lever 29, the steering mechanism 25 of the introducer 23, the anterior tube 21 and the lever 20. On the lower part of the laryngoscope the closed blades 14 and 16 are visible, as well as the ocular part of the optical system 26.

FIG. 8 represents the introducer 23 and its steering mechanism 25 taken out of the posterior tube 22 of the laryngoscope body 10. This detachment makes the cleaning and sterilisation of the introducer 23 possible. Also visible is the protrusion 29 and, in phantom lines, the endotracheal tube connector 30 with the endotracheal tube 24.

FIG. 9 is showing the frontal view of the lower part of the laryngoscope in detail. By open "beak" and its blades 14 and 16 apart, visible are the distal end of the optical system 26 and its objective, the light conducting system 27 and the distal end of the introducer 23 with the endotracheal tube 24. Further visible are the tip of the rack 33 and pinions 34 and 35 fixed on their axes on the left side of the laryngoscope body only.

FIG. 10 is showing the tube connector 30 and its protrusion lever 29 narrow enough to bypass the axes 18 and 19.

Although the particular embodiments of the invention have been shown and described in full here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A laryngoscope, comprising, an elongate body consisting of two hollow tubes, having a proximal and a distal end, two blades pivotally mounted to the distal end of said elongate body, in an angle of 90° degrees, in opposing relationship to each other, means for pivotally moving said two blades in opposing direction from each other, an elongate, flexible and steerable, tube introducing means disposed within the elongate hollow body and between the opposed blades, an endotracheal tube longitudinally disposed within said elongate hollow body and riding on said elongate, flexible and steerable tube introducing means, means for extending the tube introducing means from said elongate hollow body into the larynx and trachea, and means for introducing said endotracheal tube from said elongate hollow body into the trachea.

2. The laryngoscope of claim 1, further comprising, light conducting means for illuminating the patient's laryngeal region during intubation, optical fibers for transmitting light from a source internal or external of said laryngoscope to the laryngeal region, and said optical fibers longitudinally disposed within said elongate hollow body in substantially parallel alignment with said tube introducing means.

3. The laryngoscope of claim 1, further comprising, optical means for viewing the illuminated pharingeal region, an ocular disposed at the proximal end of said elongate hollow body parallel to the blades, and objective means comprising a system of lenses for forming an image on said ocular.

4. The laryngoscope of claim 1, said means for pivotally moving said blades relative to each other comprising, a lever, said lever disposed in angular relationship relative to said elongate hollow body so that said blades are in juxtaposition when the angle between said elongate hollow body and said lever is maximal, and so that said blades are widely spaced apart when said angle between said lever and said elongate hollow body is minimal, and bias means for urging said lever into its maximal displacement angle so that the opposed said blades are easily held in juxtaposition when said blades are introduced into a patient's mouth thereby enabling intubation of the patient unable to fully open the mouth.

5. The laryngoscope of claim 1, said means for extending said tube introducing means comprising, a lever integrally formed with said tube introducing means, said lever lying on said proximal end of said elongate hollow body so that the user of said laryngoscope easily manipulates said lever, and said proximal end of said hollow body that can be telescopically introduced into said elongate hollow body so that said tube introducing means be projected forward between said blades and into the larynx.

6. The laryngoscope of claim 1, the means for transferring said endotracheal tube from said tube introducing means and the means releasing said endotracheal tube from said tube introducing means, comprising, a lever attached to said endotracheal tube and positioned so that manually advancing said lever pushes said endotracheal tube forwardly, said lever lying on a line angled perpendicularly to the longitudinal axis of said endotracheal tube, and an elongate slot formed in the wall of said tube of said elongate hollow body so that said lever for said tube introducing means travels forwardly and rearwardly within the confines of said elongate slot.

7. The laryngoscope of claim 1, said means for pivotally moving said blades relative to each other comprising, an elongate flexible rod disposed interiorly of the distal part of said elongate hollow body, means for causing said elongate flexible rod to move linearly in a forward and rearward direction within said elongate hollow body, a rack gear having linearly spaced teeth as a part of said elongate flexible rod, a pinion gear for imparting reciprocal lineal motion to said rack gear, and said pinion gear as an integral part of said two blades.

8. A method of inserting said endotracheal tube, comprising the steps of, introducing a pair of opposed, juxtapositioned blades into the pharingeal region through a patient's partially opened mouth, increasing the spacing between said two blades only after said two blades are correctly positioned in the pharyngeal region, illuminating the patient's pharyngeal and laryngeal region, viewing the illuminated laryngeal region through said objective means, advancing said elongate, flexible and steerable tube introducing means forwardly relative to the opened blades so that the same enters the larynx, holding said endotracheal tube when the same is correctly positioned, returning said blades to their initial position, withdrawing said blades and said tube introducing means, releasing said endotracheal tube in desired position.

\* \* \* \* \*